United States Patent [19]

Gongora et al.

[11] Patent Number: 5,001,269

[45] Date of Patent: * Mar. 19, 1991

[54] PROCESS FOR THE PRODUCTION OF LOWER DIALKYL DISULPHIDES

[75] Inventors: Henri Gongora, Billere; Yves Darche, Orthez, both of France

[73] Assignee: Societe Nationale Elf Aquitaine (Production), Courbevoie, France

[ * ] Notice: The portion of the term of this patent subsequent to Oct. 24, 2006 has been disclaimed.

[21] Appl. No.: 331,760

[22] Filed: Apr. 3, 1989

[30] Foreign Application Priority Data

Apr. 14, 1988 [FR] France ................................ 88 04964

[51] Int. Cl.$^5$ .......................................... C07C 319/24
[52] U.S. Cl. ..................................................... 568/26
[58] Field of Search .......................................... 568/26

[56] References Cited

U.S. PATENT DOCUMENTS 2,237,625  4/1941  Olin ........................................ 568/26
3,299,146  1/1967  Gillette et al. ........................ 568/26

FOREIGN PATENT DOCUMENTS 0025944  4/1981  European Pat. Off. .
1358398  9/1964  France .
2130938  11/1972  France .
2607496  3/1988  France .

*Primary Examiner*—Mary E. Ceperley
*Attorney, Agent, or Firm*—Morgan & Finnegan

[57] ABSTRACT

The invention relates to the production of dialkyl disulphides of the R-SS-R type where R represents an alkyl radical having from 1 to 3 carbon atoms, by oxidation of the corresponding alkyl mercaptan R—SH by sulphur in the presence of a catalyst.

A combination of an alkyl mercantap R'—SH with an alkylene oxide and an alkaline base is used as catalyst, R' representing an alkyl radical having from 6 to 18 carbon atoms.

This catalyst enables a lower dialkyl disulphide of excellent quality to be obtained (absence of amine and coloration).

10 Claims, 1 Drawing Sheet

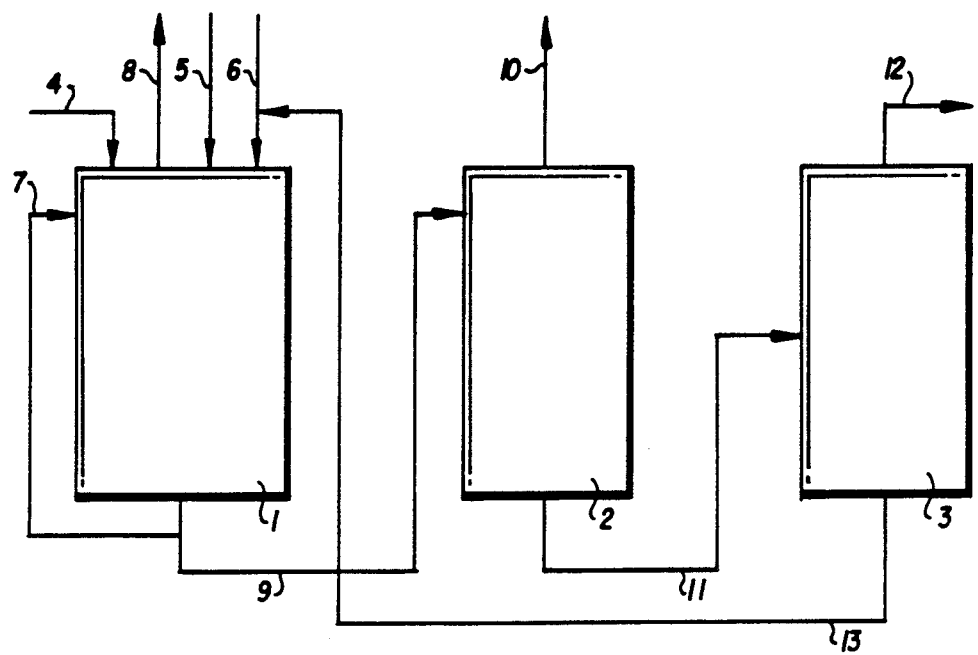

PROCESS FOR THE PRODUCTION OF LOWER DIALKYL DISULPHIDES

FIELD OF THE INVENTION

The present invention relates to organic disulphides. More particularly, its subject is the production of lower dialkyl disulphides R—SS—R where R represents an alkyl radical having from 1 to 3 carbon atoms.

BACKGROUND OF THE INVENTION

An important access route to these disulphides comprises oxidation of an alkyl mercaptan with sulphur in the presence of a catalyst in accordance with the following reaction scheme:

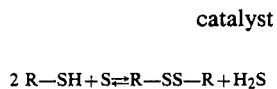

In this process, in which different secondary reactions are possible, particularly:

R—SS—R+S⇌R—SSS—R

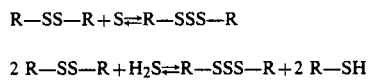

the formation of the dialkyl disulphide is promoted by an excess of alkyl mercaptan and elimination of hydrogen sulphide.

Most often aliphatic amines are used as catalysts, particularly triethylamine. See U.S. Pat. No. 2,237,625; French Patent No. 1,358,398; U.S. Pat. No. 3,299,146 and French Patent No. 2,130,985, all hereby incorporated by reference. The latter has the disadvantage of being partially retained as an impurity in the final disulphide and of giving it an undesirable coloration. Moreover, for the pretreatment of hydrocracking catalysts, some users of disulphides prefer to use products without nitrogen.

SUMMARY OF THE INVENTION

It has now been found that, without affecting the output of the production plant, it is possible to obtain a dialkyl disulphide of excellent quality, devoid of amine impurities and very weakly colored. This is done by using as catalyst the combination of a higher alkyl mercaptan R'—SH with an alkylene oxide and an alkaline base. Moreover, in a continuous production plant for dialkyl disulphide, the catalyst combination, according to the present invention, has in comparison with the trialkylamines of the prior art, the additional advantage of being recoverable and recyclable to the synthetic reactor.

DETAILED DESCRIPTION OF THE DRAWING

The FIGURE is a schematic depiction of a processing plant according to the invention.

DETAILED DESCRIPTION OF THE INVENTION

The subject of the invention is thus a process for the production of lower dialkyl disulphides R—SS—R where R represents an alkyl radical having from 1 to 3 carbon atoms. This is done by oxidation of the corresponding alkyl mercaptan R—SH with sulphur in the presence of a catalyst. The catalyst used is a combination of a higher alkyl mercaptan R'—SH with an alkylene oxide and an alkaline base. It is possible to represent this combination by the formula

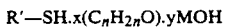

in which R' is a linear or branched alkyl radical, having from 6 to 18 carbon atoms, n is a number in the range 2 to 4, x is a number in the range 1 to 20, y is a number in the range 0.01 to 1 and M represents an alkali metal atom. It is preferably Na or K.

The preferred combinations are those in which R' is a $C_8-C_{16}$ tertiary alkyl radical (for example tert-nonyl or tertdodecyl), the number x of moles of alkylene oxide per mole of mercaptan R'—SH is between 4 and 12, and the number y of moles of alkaline base is between 0.1 and 0.5. As alkylene oxide, it is preferable to use the more economic ethylene oxide. If desired, it may be replaced by or mixed with propylene oxide or butylene oxide.

One method of production of the catalyst combination according to the invention comprises initially mixing 1 mole of mercaptan R'SH with αy moles (α=1 to 1.5) of alkaline base MOH. Preferably, this mixture is homogenized while hot. This operation can be carried out in a few hours between 50° and 100° C., in particular in 4 to 6 hours between 75° and 85° C. Into the liquid obtained in this manner, is subsequently injected the alkylene oxide $C_n H_{2n}O$ so as to incorporate the desired proportion x. This injection is preferably carried out under 0.2 to 4 bars and at a temperature of 80° to 120° C. depending on the nature of the mercaptan R'SH used. The incorporation of the alkylene oxide generally takes from 1 to 10 hours. After these operations, it is advisable to eliminate the excess alkylene oxide by degassing from the reaction mixture using an inert gas such as nitrogen. Then, the liquid obtained is filtered before using it as catalyst in the process according to the invention.

The quantity of catalyst to be used for the oxidation reaction producing disulphides RSSR may be in the range 0.2 to 5% in relation to the weight of sulphur used and is preferably between 1.5 and 4%.

As in the known processes, the molar ratio mercaptan RSH/sulphur must be at least equal to 2 and is preferably between 3 and 5.

The oxidation reaction may be carried out at a temperature in the range of 25° to 125° C. under an effective pressure in the range 1 to 5 bars, preferably between 3 and 4 bars. The optimal temperature depends on the mercaptan RSH used; it is 50°-60° C. for methyl mercaptan, 60°-70° C. for ethyl mercaptan and 70°-80° C. for propyl mercaptan.

Although the catalyst combination according to the invention may be used in a discontinuous process for the production of dialkyl disulphides R—SS—R, it is intended more particularly for the production of these dialkyl disulphides in a plant operating a continuous process.

The appended diagram is a schematic representation of a processing plant of this type. It comprises particularly a reactor 1, a degassing column 2 and a distillation column 3.

The reactants: liquid sulphur, mercaptan RSH (liquid or gaseous) and catalyst (or recycled bottoms originating from the base of column 3) are continuously added through the pipes 4, 5 and 6 respectively into the reactor 1. It is provided with the usual regulation devices for temperature, pressure, level and an external recycling loop 7 which ensures that mass and heat transfers can occur. The residence time of the reactants in this reactor may be in the range 20 to 180 minutes. It is preferably between 30 and 90 minutes and is advantageously about one hour. The gaseous effluents are eliminated from the head of the reactor by the pipe 8 to the flaring line. The crude reaction liquid, drawn from the base of the reactor, is fed to the degassing column 2 through the line 9.

This packed column, provided with hot water circulation and an inlet for inert gas such as methane or nitrogen, enables the greater part of the hydrogen sulphide coproduced and of the excess of alkyl mercaptan RSH to be separated. The latter is subsequently fed through the pipe 10 into a heat exchanger-condenser where it is condensed before being recycled to the reactor 1 either directly, or via a storage tank. At the base of column 2, a crude product is recovered comprising the desired dialkyl disulphide RSSR, corresponding polysulphides (mainly dialkyl trisulphide), the catalyst and a small amount of alkyl mercaptan.

This crude product is fed through the line 11 into the column 3 where it is distilled under reduced pressure. The desired dialkyl disulphide is recovered at the head through the line 12, while the bottoms comprising mainly a mixture of dialkyl disulphide, dialkyl trisulphide and catalyst are recycled to the reactor 1 through the lines 13 and 6.

The following example illustrates the invention without limiting it.

EXAMPLE (a) Preparation of the catalyst

To a 150 liter stainless steel reactor, are added 68 kg (336.6 moles) of tert-dodecyl mercaptan $C_{12}H_{25}SH$ with 6.3 kg (157.5 moles) of anhydrous NaOH. Then good dispersion and homogenization of the mixture are ensured by heating at 80° C. for 5 hours. Subsequently, ethylene oxide is injected into the reactor with a continuous output rate of 7 kg/h for 8 hours. The relative pressure in the reactor changes from 0.2 bar initially to 4 bars at the end of the addition. The reaction mixture is subsequently heated at 100°-110° C. for 2 hours, then decompressed and degassed by means of a current of nitrogen to eliminate all the dissolved excess ethylene oxide. The liquid obtained is then subjected to a filtration to remove solid particles greater than 5 μm.

The catalyst combination in this manner has the following molar composition:

$C_{12}H_{25}SH, 6(CH_2CH_2O), 0.35NaOH$ which is by weight:

| | |
|---|---|
| $C_{12}H_{25}SH$ | 42% |
| $CH_2CH_2O$ | 55% |
| NaOH | 3% |

The cloud point of this catalyst is at about 62° C.

(b) Continuous synthesis of dimethyl disulphide (DMDS)

The operation is carried out in a plant of the type described above. The reactor 1 is fed continuously with 10 kg/h of liquid sulphur, 55 kg/h of liquid methyl mercaptan and 0.35 kg/h of the catalyst obtained as described in paragraph (a). When the reaction has reached equilibrium (after about 12 hours), this feed of 0.35 kg/h of catalyst is replaced by recycling, at the rate of 7 kg/h, of the product originating from the bottom of distillation column 3. It contains 0.35 kg of catalyst, 3.64 kg of DMDS and 3.01 kg of polysulphides, mainly of dimethyl trisulphide (DMTS).

The reaction is carried out in the region of 55°-58° C. under an effective pressure of 3.5 bars. The average residence time of the reactants in the reactor is about one hour. The crude reaction liquid coming out of the reactor is fed into column 2 where it is subjected to degassing in the region of 65°-70° C. using a current of 6 $Nm^3/h$ of commercial gas (methane).

From the base of column 2, is recovered 37.26 kg/h of a liquid containing by weight 85.70% of DMDS, 12.23% of DMTS, 1.13% of methyl mercaptan and 0.94% of catalyst. This liquid is fed into distillation column 3 where it is fractionated under the following conditions:

| | |
|---|---|
| feed output | about 37 kg/h |
| distillation output | about 28.1 kg/h |
| bottoms output | about 8.5 kg/h |
| partial pressure at the head | 13.33 kPa |
| head temperature | 56° C. |
| bottoms temperature | 90°-100° C. |

At the head of the column, 28.1 kg/h of DMDS are obtained having a purity of 99%, which is a yield of 95% in relation to the sulphur used. The DMDS produced in this way is very weakly colored It is devoid of amine impurities, sodium hydroxide and oxygen. Its residual $CS_2$ content is less than 500 ppm.

From the base of the column, 8.3 kg/h are recovered of a mixture containing by weight about 43.85% of DMDS, 29.05% of DMTS, 4.2% of catalyst and 22.9% of higher polysulphides. After filtration, 7 kg/h are obtained of a product containing about 5% of catalyst, 52% of DMDS and 34.4% of DMTS. Once reaction equilibrium is reached, this product is introduced as a replacement for fresh catalyst.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for the production of a lower dialkyl disulphide of formula R—SS—R where R represents an alkyl radical having from 1 to 3 carbon atoms, comprising oxidation of the corresponding alkyl mercaptan RSH with sulphur in the presence of a catalyst, the catalyst used is a combination of a higher alkyl mercaptan R'—SH with an alkylene oxide $C_nH_{2n}O$ and an alkaline base MOH, this combination is represented by the formula

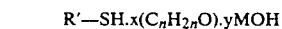

$R'—SH.x(C_nH_{2n}O).yMOH$ in which R' is a linear or a branched alkyl radical containing from 6 to 18 carbon atoms, n is a number in the range 2 to 4, x is a number in the range 1 to 20, y is a number in the range 0.01 to 1 and M represents an alkali metal atom whereby the dialkyl disulphide is substantially devoid of amine impurities and very weakly colored and the catalyst being recoverable and recyclable.

2. The process according to claim 1, wherein R' is a $C_8$-$C_{16}$ tertiary alkyl radical, preferably tert-nonyl or tertdodecyl.

3. The process according to claim 1, wherein n is equal to 2, x is between 4 and 12 and y is between 0.1 and 0.5.

4. The process according to claim 1, wherein the catalyst is used in a quantity of 0.2 to 5% in relation to the weight of sulphur added, the molar ratio mercaptan RSH/sulphur being at least equal to 2.

5. The process according to claim 1, wherein the molar ratio mercaptan RSH/sulphur is between 3 and 5.

6. The process according to claim 1, wherein the reaction is carried out at a temperature in the range 25° to 125° C. and under an effective pressure in the range 1 to 5 bars.

7. The process according to claim 6, wherein the temperature range is between 50° and 80° C. and the pressure range is between 3 and 4 bars.

8. The process according to claim 1, wherein operation is continuous, residence time in the reactor is in the range 20 to 180 minutes.

9. The process according to claim 8, wherein the residence time is between 30 and 90 minutes.

10. The process according to claim 1, wherein the alkyl mercaptan RSH is methyl mercaptan.

* * * * *